(12) United States Patent
Bang et al.

(10) Patent No.: US 9,894,441 B2
(45) Date of Patent: *Feb. 13, 2018

(54) METHOD AND APPARATUS FOR CUSTOMIZING AUDIO SIGNAL PROCESSING FOR A USER

(71) Applicant: Samsung Electronics Co., Ltd., Gyeonggi-do (KR)

(72) Inventors: Kyoungho Bang, Seoul (KR); Yangsu Kim, Gyeonggi-do (KR); Kyungseok Oh, Seoul (KR); Juntai Kim, Gyeonggi-do (KR); Gunhyuk Yoon, Gyeonggi-do (KR); Chulmin Choi, Seoul (KR)

(73) Assignee: Samsung Electronics Co., Ltd (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/355,732

(22) Filed: Nov. 18, 2016

(65) Prior Publication Data
US 2017/0070818 A1    Mar. 9, 2017

Related U.S. Application Data

(63) Continuation of application No. 14/034,016, filed on Sep. 23, 2013, now Pat. No. 9,532,154.

(30) Foreign Application Priority Data

Sep. 21, 2012    (KR) .......................... 10-2012-0104861

(51) Int. Cl.
*H04R 3/04*    (2006.01)
*H04R 29/00*    (2006.01)
(Continued)

(52) U.S. Cl.
CPC .............. *H04R 3/04* (2013.01); *A61B 5/123* (2013.01); *G06F 3/165* (2013.01);
(Continued)

(58) Field of Classification Search
CPC ........ G06F 17/289; H04R 3/04; H04R 29/002
(Continued)

(56) References Cited

U.S. PATENT DOCUMENTS 5,982,901 A    11/1999    Kane
6,115,589 A    9/2000    Ferrer
(Continued)

FOREIGN PATENT DOCUMENTS

KR    1020120069813    6/2012

*Primary Examiner* — Gerald Gauthier
(74) *Attorney, Agent, or Firm* — The Farrell Law Firm, P.C.

(57) ABSTRACT

A method and an apparatus for customizing audio data processing are provided. The method includes receiving audio data through a wireless communication channel from an external device; decoding the received audio data; reducing noise of the decoded audio data; identifying hearing characteristics of a user by testing hearing abilities of the user at a plurality of frequency bands; adjusting a dynamic range of each of the plurality of frequency bands based on the hearing characteristics; processing the noise-reduced audio data based on the adjusted dynamic range of each of the plurality of frequency bands; and outputting the processed audio data.

18 Claims, 10 Drawing Sheets

(51) Int. Cl.
  *H04R 3/00* (2006.01)
  *A61B 5/12* (2006.01)
  *G06F 3/16* (2006.01)
  *G10L 21/0232* (2013.01)
  *H04R 25/00* (2006.01)

(52) U.S. Cl.
  CPC ............ *G10L 21/0232* (2013.01); *H04R 3/00* (2013.01); *H04R 29/00* (2013.01); *H04R 25/70* (2013.01); *H04R 2420/07* (2013.01); *H04R 2430/03* (2013.01); *H04R 2499/11* (2013.01)

(58) Field of Classification Search
  USPC ...... 381/56, 79, 94.3, 98, 314, 315, 330, 57, 381/74, 104; 455/296, 563; 600/554
  See application file for complete search history.

(56) References Cited

U.S. PATENT DOCUMENTS

| | | | |
|---|---|---|---|
| 6,438,245 B1* | 8/2002 | Taenzer | H04M 1/05 381/322 |
| 6,690,805 B1 | 2/2004 | Tsuji | |
| 6,813,490 B1 | 11/2004 | Lang | |
| 7,027,591 B2 | 4/2006 | Cairns | |
| 7,225,001 B1 | 5/2007 | Eriksson | |
| 7,403,611 B1 | 7/2008 | He | |
| 7,925,237 B2* | 4/2011 | Kim | H04M 9/08 455/296 |
| 8,457,688 B2* | 6/2013 | Stenmark | H04M 1/6016 381/312 |
| 8,792,661 B2* | 7/2014 | Apfel | H04R 25/305 381/314 |
| 9,173,045 B2* | 10/2015 | Bruss | H04R 1/1091 |
| 9,613,028 B2* | 4/2017 | Foo | G06F 17/289 |
| 2002/0111796 A1 | 8/2002 | Nemoto | |
| 2004/0208325 A1* | 10/2004 | Cheung | H04S 1/00 381/79 |
| 2006/0140418 A1 | 6/2006 | Koh et al. | |
| 2006/0222185 A1* | 10/2006 | Dyer | H04R 29/001 381/74 |
| 2008/0025538 A1* | 1/2008 | Zad-Issa | H04R 25/43 381/315 |
| 2008/0037797 A1* | 2/2008 | Goldstein | A61B 5/121 381/56 |
| 2008/0130916 A1* | 6/2008 | Kong | H03G 3/3026 381/104 |
| 2008/0137873 A1* | 6/2008 | Goldstein | H04R 1/1016 381/57 |
| 2008/0159547 A1* | 7/2008 | Schuler | G01H 3/14 381/56 |
| 2012/0157876 A1 | 6/2012 | Bang et al. | |
| 2012/0183164 A1* | 7/2012 | Foo | H04R 25/70 381/314 |
| 2012/0183165 A1* | 7/2012 | Foo | H04R 25/50 381/314 |
| 2013/0148818 A1* | 6/2013 | Yamkovoy | H04R 1/1041 381/74 |
| 2013/0163797 A1* | 6/2013 | Suzman | H04R 25/50 381/314 |
| 2013/0202130 A1* | 8/2013 | Zurek | H04M 1/6008 381/94.3 |
| 2013/0216052 A1 | 8/2013 | Bruss et al. | |
| 2014/0086434 A1* | 3/2014 | Bang | A61B 5/123 381/98 |

* cited by examiner

FIG. 6
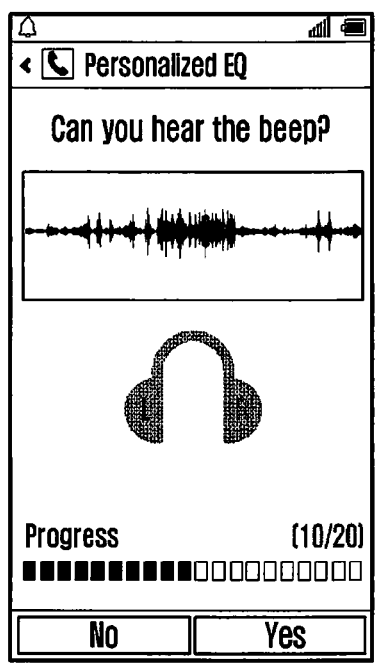
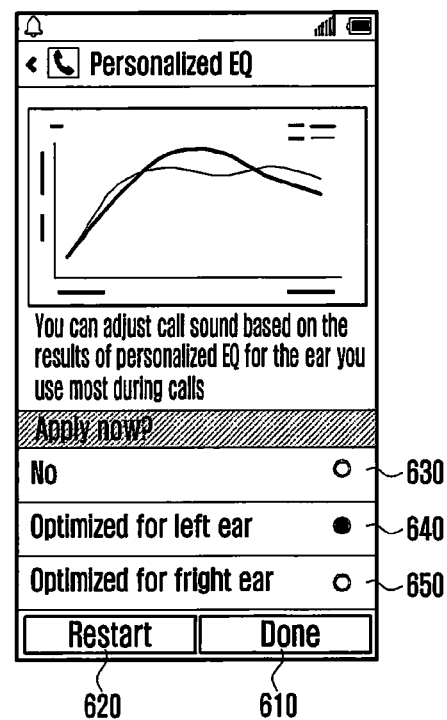

METHOD AND APPARATUS FOR CUSTOMIZING AUDIO SIGNAL PROCESSING FOR A USER

PRIORITY

This application is a continuation of U.S. Ser. No. 14/034,016, which was filed in the U.S. Patent and Trademark Office on Sep. 23, 2013, and claims priority under 35 U.S.C. § 119(a) to Korean Patent Application Serial No. 10-2012-0104861, which was filed in the Korean Intellectual Property Office on Sep. 21, 2012, the entire disclosure of which is incorporated herein by reference.

BACKGROUND OF THE INVENTION

1. Field of the Invention

The present invention relates generally to improving audio quality, and more particularly, to a method and mobile device that customize audio signal processing based on hearing characteristics of a particular user.

2. Description of the Related Art

Typically, a mobile device stores data corresponding to an audio signal in the mobile device, or receives an audio signal via a radio communication transceiver, decodes the audio signal, processes the decoded audio signal such as cancelling noise from the decoded audio signal, and outputs the noise-canceled audio data through a speaker or an external device interface (e.g., earphone jack or Bluetooth connection).

However, a conventional mobile device outputs the audio data at a fixed quality, which is configured by a manufacturer of the mobile device.

More specifically, in order to improve quality, the conventional mobile device uses a noise reduction technique, a sound pressure control technique, etc. However, a user's hearing characteristics are not reflected in the audio signal processing such as noise reduction and sound pressure control techniques because the quality is fixed to a predetermined level.

Accordingly, an audio signal that is adjusted to the fixed quality may not be suitable for all users. That is, because users have different hearing characteristics, audio provided by a mobile device will be experienced differently by each of the users.

Further, the number of hearing-impaired persons is increasing every year. One of probable causes of this increase is the frequent use of audio devices such as an MP3 player or a headset at excessively loud levels.

SUMMARY OF THE INVENTION

Accordingly, the present invention is designed to address at least the problems and/or disadvantages described above and to provide at least the advantages described below.

An aspect of the present invention is to provide a method and mobile device for customizing audio processing for a user of the mobile device.

Another aspect of the aspect of the present invention is to provide a method and mobile device that test hearing abilities and characteristics of a user.

Another aspect of the aspect of the present invention is to provide a method and mobile device that customize audio processing for a user based on tested hearing abilities and characteristics of the user.

In accordance with an aspect of the present invention, a method is provided for customizing audio data processing. The method includes receiving audio data through a wireless communication channel from an external device; decoding the received audio data; reducing noise of the decoded audio data; identifying hearing characteristics of a user by testing hearing abilities of the user at a plurality of frequency bands; adjusting a dynamic range of each of the plurality of frequency bands based on the hearing characteristics; processing the noise-reduced audio data based on the adjusted dynamic range of each of the plurality of frequency bands; and outputting the processed audio data.

In accordance with another aspect of the present invention, an apparatus is provided for customizing audio data processing. The apparatus includes a radio communication unit which receives audio data through a wireless communication channel from an external device; a speaker; and a controller configured to decode the audio data received by the radio communication unit, reduce noise of the decoded audio data, test hearing characteristics of a user at a plurality of frequency bands, adjust a dynamic range of each of the plurality of frequency bands based on results of the testing, adjust the noise-reduced audio data based on the adjusted dynamic range of each of the plurality of frequency bands, and output the adjusted audio data to the user via the speaker.

BRIEF DESCRIPTION OF THE DRAWINGS

The above and other aspects, features, and advantages of certain embodiments of the present invention will be more apparent from the following detailed description taken in conjunction with the accompanying drawings, in which:

FIG. 6 illustrates examples of screens displayed to a user during a hearing ability test according to an embodiment of the present invention;

DETAILED DESCRIPTION OF EMBODIMENTS OF THE INVENTION

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

In the following description, a mobile device may be any device equipped with a radio communication device for voice telephony, such as a smartphone, a tablet Personal Computer (PC), a laptop PC, a desktop PC, a video phone, etc.

Figure 1:
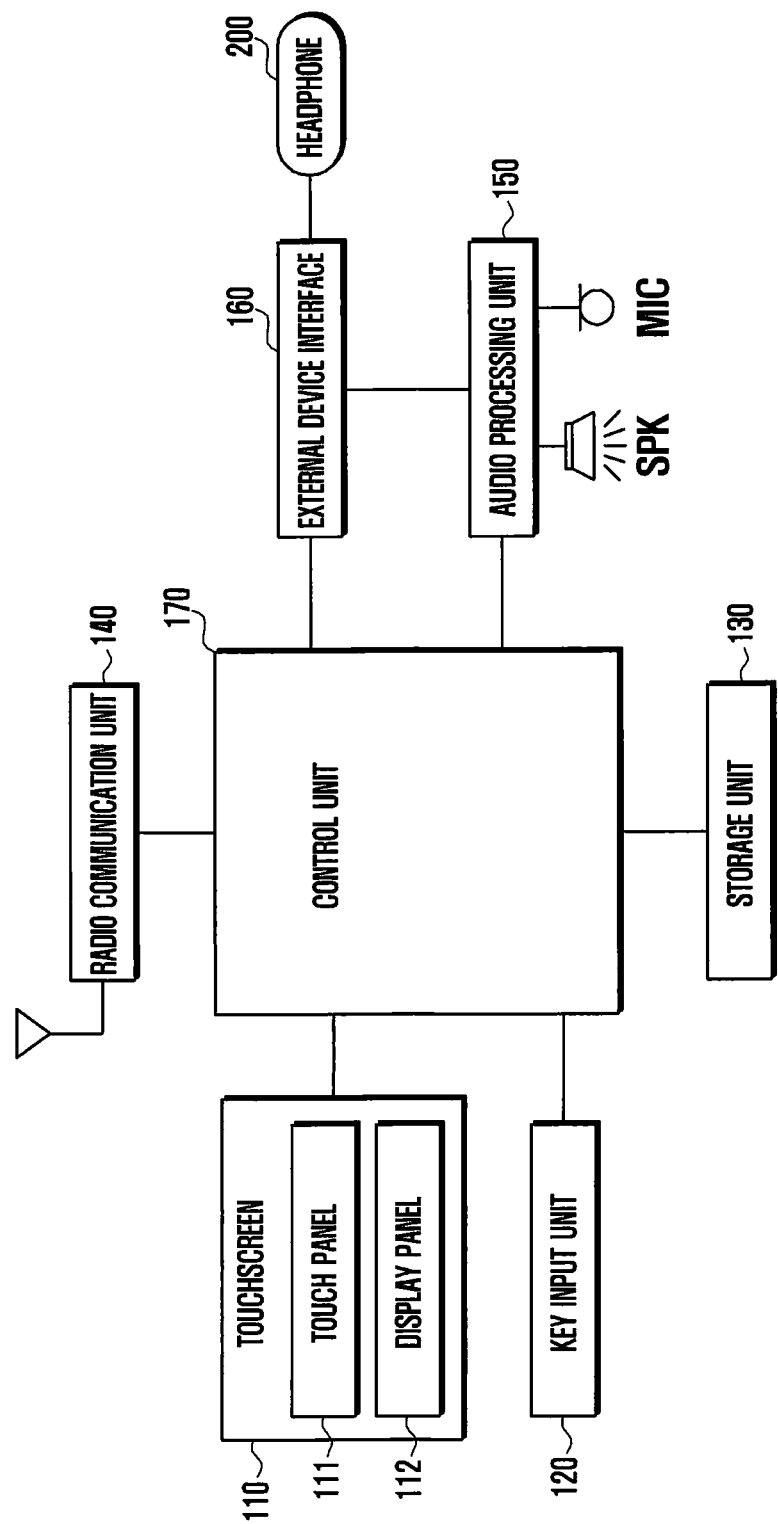
FIG. 1 illustrates a mobile device according to an embodiment of the present invention.

FIG. 1 illustrates a mobile device according to an embodiment of the present invention.

Referring to FIG. 1, the mobile device includes a touchscreen 110, a key input unit 120, a storage unit 130, a radio communication unit 140, an audio processing unit 150, a speaker (SPK), a microphone (MIC), an external device interface 160, and a control unit 170.

The touchscreen 110 facilitates interaction with the user and includes a touch panel 111 and a display panel 112. The touch panel 111 can be placed on the display panel 112. The touch panel generates an analog signal (e.g. touch signal) corresponding to a user gesture made on the touch panel 111 and processes the analog signal to generate a digital signal to the control unit 170. The control unit 170 is aware of the user gesture based on the touch signal from the touch panel 111. The user gesture is classified into one of a touch and a touch gesture. The touch gesture includes a 'tap', 'drag', 'flick', etc. The term 'touch' denotes a state where an object contacts the surface of the touchscreen 110, and the term 'touch gesture' denotes a state change of the touch from the touch-on instant to the touch-off instant. The touch panel may be implemented as a combination of a finger touch panel and a pen touch panel. Here, the finger touch panel is a capacitive type touch panel, but can also be one of a resistive type, an infrared type, a microwave type, etc., touch panels. The finger touch panel may be configured to generate an input signal in response to a touch gesture made with an object (e.g. a conductive material capable of changing the capacitance amount) as well as the user's finger. The pen touch panel may be an electromagnetic induction type. In this case, the pen touch panel generates an input signal in response to the touch gesture made with a touch input tool, such as a stylus pen, capable of generating a magnetic field.

The display panel 112 converts the video data input by the control unit 170 to an analog signal under the control of the control unit 170. That is, the display panel 112 displays various screen pictures, e.g. a device lock screen, home screen, settings screen, application (App) execution screen, a keypad, and the like. The device lock screen is displayed when the display panel 112 turns on. If a user gesture for unlocking the device is detected, the control unit 170 is capable of switching the device lock screen to the home screen or application execution screen. The home screen has a plurality of icons corresponding to the respective applications (e.g. settings, browser, telephony, and message applications). If one of the application icons is selected (tapped) by the user, the control unit 170 executes the corresponding application and controls the display panel 112 to display the execution screen of the application. The display panel 112 displays one of the screens (e.g. a page of home screen) as a background image and another (e.g. keypad) as a foreground image on the background image under the control of the control unit 170. The display panel 112 is also capable of displaying multiple screens without overlapping among each other under the control of the control unit 170. For example, the display panel 112 is capable of displaying one of the screens in a first screen region and another in a second screen region. The display panel 112 can be implemented with a Liquid Crystal Display (LCD), an Organic Light Emitted Diode (OLED), or an Active Matrix OLED (AMO-LED).

The key input unit 120 is provided with a plurality of keys (buttons) for inputting alphanumeric information and configuring various functions. These keys may include a menu call key, screen on/off key, power on/off key, volume control key, etc. The key input unit 120 generates key event signals related to user settings and device function controls to the control unit 170. The key events may include power on/off event, volume control event, screen on/off event, etc. The control unit 170 controls the components in response to the key event signals. The keys (buttons) provided by the key input unit 120 can be referred to as hard keys (buttons) while those provided by the touchscreen 110 as soft keys (buttons). The key input unit 120, e.g., a keypad, is provided with a plurality of keys (buttons) for inputting various user inputs such as volume control and setting ON/OFF customizing audio signal processing.

The storage unit 130, e.g., a memory device, may include a disc, a Random Access Memory (RAM), a Read Only Memory (ROM), a flash memory, etc. The storage unit 130 stores data generated in and received by the mobile device.

Particularly, the storage unit 130 stores hearing ability test sounds, which are output to a user (e.g., through the speaker (SPK) or headphones 200). When outputting test sounds though the headphones 200, a user's right ear and left ear can each be tested during a single test. However, when outputting test sounds though the speaker (SPK), a separate test will have to be performed for a user's right ear and left ear.

The test sounds may be classified by frequency and sound pressure. For example, when using 6 frequencies of 250 Hz, 500 Hz, 1 kHz, 2 kHz, 4 kHz, and 8 kHz and 8 sound pressure levels from 0 to 80 dB at an interval of 10 dB, i.e., 10 db, 20 dB, 30 dB, . . . , 80 dB, a total of 48 test sounds are stored in the storage unit 130.

Although the description below uses 6 frequencies and 8 sound pressure levels, the present invention is not limited thereto. The test sounds may be generated at any frequency in the audible frequency range and at any sound pressure level, even over 80 dB. Also, the interval of the sound pressure level may differ, e.g., may be 5 dB.

Herein, the term "test sound pressure" refers to the sound pressure level converted in units of decibels Hearing Level (dBHL). Further, the term "test frequency" refers to the frequency of the test sound, and the term "test sound pressure range" refers to the range of the test sound pressure configurable for a test sound. That is, the sound pressure level of the test sound can be configured in the range of a configurable test sound level range.

The storage unit 130 stores a parameter (auditory threshold, i.e., a minimum sound level that is audible with normal hearing) for changing the dynamic range per frequency. Here, the dynamic range denotes the difference (rate) between the loudest sound pressure and weakest sound in the received audio signal. Users may have dynamic ranges depending on their hearing characteristics.

The storage unit 130 stores an Operating System (OS) for operating the mobile device and various programs.

Particularly, the storage unit 130 stores a hearing ability test program for checking an auditory threshold and an audio signal processing program for processing the received audio signal.

In accordance with an embodiment of the present invention, various hearing ability test programs may be used, e.g., a descending method program, an ascending method program, a hybrid method program, and a binary search method program. The descending method program measures auditory thresholds in order from a highest level to a lowest level for each frequency in a stepwise manner. The ascending method program measures auditory thresholds in order from a lowest level to a highest level in a stepwise manner. The hybrid method program compensates for differences between auditory threshold decisions of the descending and ascending method programs. That is, the hybrid method program performs the ascending method program to determine an initial auditory threshold and then performs the descending method program to determine the final auditory threshold, or performs the descending method program to determine the initial auditory threshold and then the ascending method program to determine the final auditory threshold.

Figure 2:
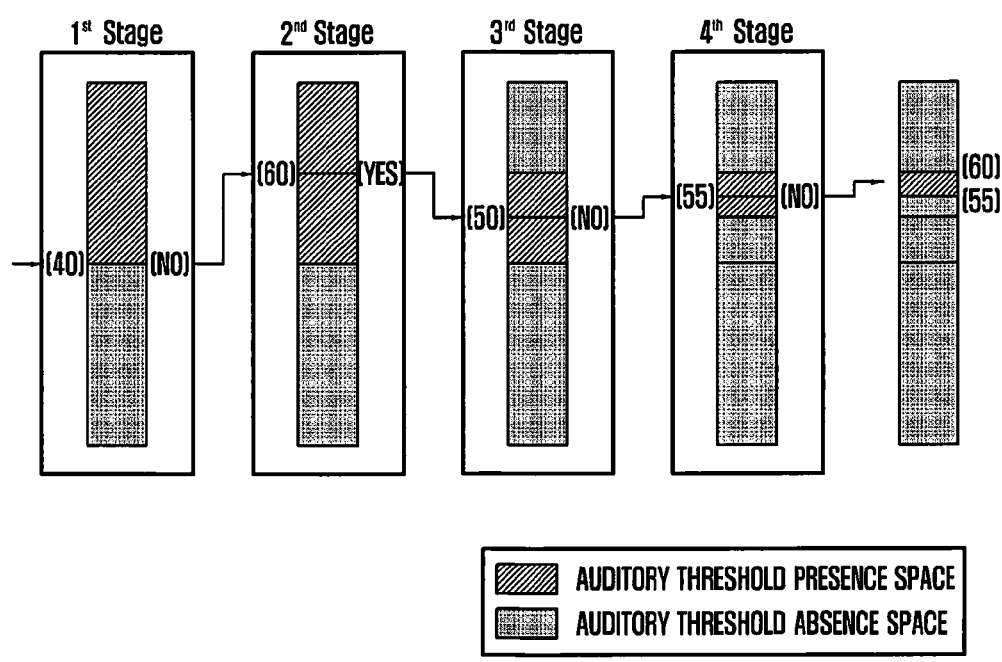
FIG. 2 illustrates a binary search method according to an embodiment of the present invention.

FIG. 2 illustrates a binary search method according to an embodiment of the present invention.

Referring to FIG. 2, the control unit 170 performs a test on the corresponding test frequency a number of times, e.g., 4 times (stages), and when the potential auditory threshold existence space (or range) decreases to 5 dB or less, stops the binary search and determines the corresponding space (e.g., 55 to 60 dB) as the auditory threshold for the corresponding test frequency.

Specifically, in FIG. 2, at the first stage, the range of 0 dB to 80 dB is divided in half into a region at or below 40 dB and a region above 40 dB, and a test signal is output at 40 dB. Because the user cannot hear the test signal at 40 dB, the region at or below 40 dB is determined as an auditory threshold absence space, and the region above 40 dB is determined as an auditory threshold presence space.

Because the potential auditory threshold is located in the range greater than 40 bB to 80 dB, at the second stage, this range is then divided in half into a region at or below 60 dB and a region above 60 dB, and a test signal is output at 60 dB. Because the user can hear the test signal at 60 dB, the region at or below 60 dB is determined as an auditory threshold presence space, and the region above 60 dB is determined as an auditory threshold absence space.

Because the potential auditory threshold is located in the range greater than 40 bB to 60 dB, at the third stage, this range is then divided in half into a region at or below 50 dB and a region above 50 dB, and a test signal is output at 50 dB. Because the user cannot hear the test signal at 50 dB, the region at or below 50 dB is determined as an auditory threshold absence space, and the region above 50 dB is determined as an auditory threshold presence space.

Because the potential auditory threshold is located in the range greater than 50 bB to 60 dB, at the fourth stage, this range is then divided in half into a region at or below 55 dB and a region above 55 dB, and a test signal is output at 55 dB. Because the user cannot hear the test signal at 55 dB, the region at or below 55 dB is determined as an auditory threshold absence space, and the region above 55 dB is determined as an auditory threshold presence space.

Further, because the range of 55 dB to 60 dB is 5 dB or less, the corresponding space is determined as the auditory threshold for the corresponding test frequency.

The received audio signal processing program includes functions for decoding the audio signal received by the radio communication unit 140, performing noise reduction (or noise suppression) and noise gating on the decoded audio signal, adjusting the dynamic range per frequency with the parameter (i.e., auditory threshold), and changing the received audio signal using the adjusted dynamic range for each frequency. For example, assuming an auditory threshold of 20 dB for the user at a frequency of 1 kHz, the received audio signal processing program may change the dynamic range of 1 kHz component of the received audio signal from 0-80 dB to 20-80 dB. If so, when the 1 kHz frequency component of the received signal has a size of 10 dB, the size of the 1 kHz frequency component of the received signal may be changed from 10 dB to 20 dB or more within the adjusted dynamic range.

The storage unit 130 may store the embedded applications and third party applications. The embedded applications denote the applications installed on the mobile terminal 100. For example, the embedded application can be any of browser, email, instant messenger, etc., applications. The third party applications are applications that can be downloaded from online markets and installed on the mobile terminal 100. The third party applications can be installed and uninstalled whenever necessary. Once the mobile terminal 100 turns on, the booting program is loaded on the main memory (e.g. RAM) of the control unit 170. The booting program loads the OS of the mobile terminal on the main memory. The OS loads and executes various programs on the main memory. In particular, when the telephone function is activated, the OS loads and executes the audio signal processing program on the main memory. Since the terminal booting and program loading procedures are well-known in the computer system field, a detailed description thereof is omitted herein.

Referring again to FIG. 1, the radio communication unit 140 is responsible for voice telephony, video telephony, and data communication under the control of the control unit 170. For example, the radio communication unit 140 includes a Radio Frequency (RF) transceiver for up-converting and amplifying a signal to be transmitted and low noise amplifying and down-converting a received signal. The radio communication unit 140 may include a cellular communication transceiver (e.g., $3^{rd}$ Generation (3G), 3.5G, and 4G cellular communication), a digital broadcast transceiver (e.g., DMB), and a short range communication transceiver (e.g., Wi-Fi or Bluetooth).

The audio processing unit 150 may include the speaker (SPK) and the microphone (MIC) to support voice recognition, voice recording and audio input/output for voice communication. The audio processing unit 150 converts the analog audio signal received through the microphone (MIC) to a digital audio signal and sends the digital audio signal to the control unit 170. The speaker outputs an audio sound wave, and the microphone (MIC) receives a human voice or other sound.

The external device interface 160, e.g., a headphone jack, is provided to attach an external device, e.g., headphones 200. The external device interface 160 may also connect the headphones 200 to the mobile device using short range communication (e.g., Bluetooth).

The control unit 170 controls overall operations of the mobile device. For example, the control unit 170 includes a storage device for storing application programs and an OS, a cache memory for caching data to be stored in the storage unit 130 and read from the storage unit 130, a Central Processing Unit (CPU), and a Graphic Processing Unit (GPU). The CPU and GPU can be integrated into a package as a multi core (e.g., quad-core) single integrated circuit, in the form of System on Chip (SoC), or in the form of a multi-layer package. The CPU and GPU may be referred together as an Application Processor (AP).

Figure 3:
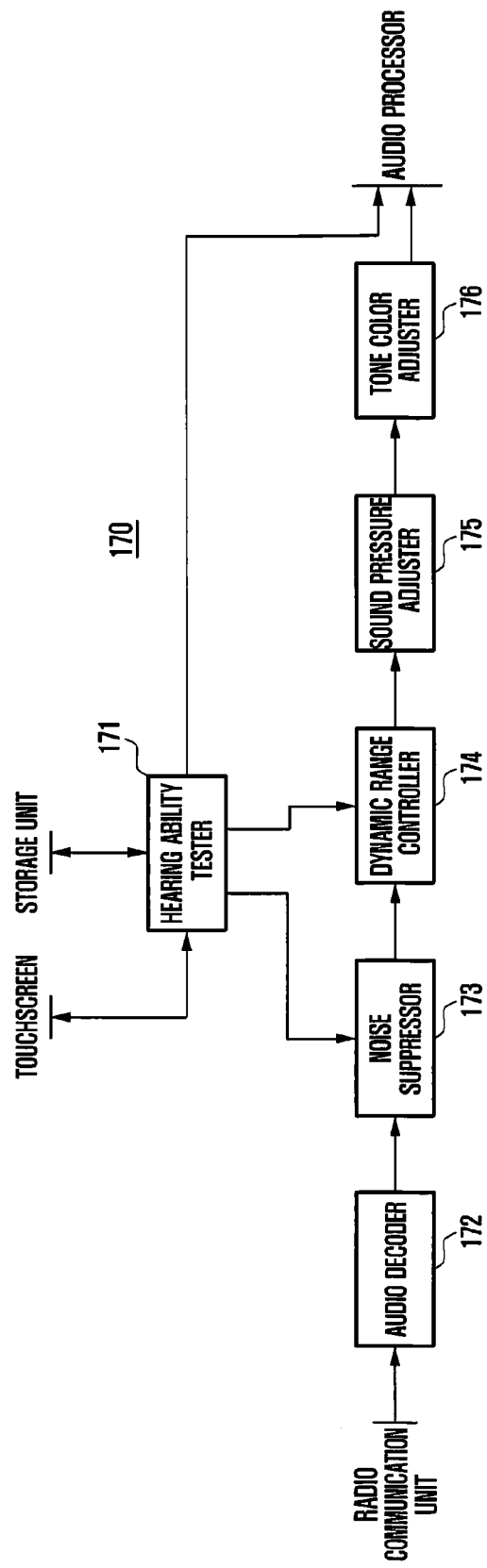
FIG. 3 illustrates a conceptual operation of a control unit of a mobile device according to an embodiment of the present invention.

FIG. 3 illustrates a conceptual operation of a control unit of a mobile device according to an embodiment of the present invention.

Referring to FIG. 3, the control unit 170 performs functions of a hearing ability tester 171, an audio decoder 172, a noise suppressor 173, a dynamic range controller 174, a sound pressure adjuster 175, and a tone color adjuster 176.

The hearing ability tester 171 tests the hearing ability of a user and determines an auditory threshold for each frequency. Particularly, the hearing ability tester 171 performs the binary search method to determine a user's auditory threshold.

More specifically, the hearing ability tester 171 selects a test frequency among plural candidate test frequencies (e.g., 250 Hz, 500 Hz, 1 kHz, 2 kHz, 4 kHz, and 8 kHz). Herein, the test frequency may be selected randomly or in an ascending or descending order. The hearing ability tester 171 reads the test sound pressure ranges configured for the respective frequencies from the storage unit 130 and selects the test sound pressure based on the test sound pressure ranges. For example, when the test sound pressure range for 1 kHz is 0 dB to 80 dB, the hearing ability tester 171 reads the selected test frequency and the test sound corresponding to the selected test sound pressure from the storage unit 130 and outputs them to the audio processing unit 150. The audio processing unit 150 performs D/A conversion on the test sound to output the analog signal to the speaker (SPK) or the headphone 200 through the external device interface 160.

The hearing ability tester 171 stores a user response to a test sound in the storage unit 130. For example, if a user hears a test sound of [1 kHz, 40 dB], the hearing ability tester 171 stores [1 kHz, −40 dB]. However, if the user does not hear the test sound, then [1 kHz, +40 dB] is stored in the storage unit 130. Here, "−" indicates that the auditory threshold exists below 40 dB in the test sound pressure range, and "+" indicates that the auditory threshold exists above 40 dB. The hearing ability tester 171 reconfigures the test sound pressure range of the test frequency, e.g., as illustrated in FIG. 2.

More specifically, according to the user response to the test sound, the hearing ability tester 171 divides the currently-configured test sound pressure range into one region having the auditory threshold and another region having no auditory threshold. Thereafter, the hearing ability tester 171 reconfigures the region having the auditory threshold as a new test sound pressure range and stores the new test source pressure range in the storage unit 130. If the difference between the highest and lowest levels of the reconfigured test sound pressure range is less than or equal to a predetermined minimum range (e.g., 5 dB), the hearing ability tester 171 determines the reconfigured test sound pressure range as the auditory threshold of the test frequency.

The hearing ability tester 171 can determine either the highest level, the lowest level, or the average of the highest and lowest levels as the auditory threshold. For example, if the reconfigured test sound pressure range is 50 dB to 55 dB, the hearing ability tester 171 can determine the auditory threshold to be 55 dB, 50 dB, or 52.5 dB.

The audio decoder 172 receives the audio signal from the radio communication unit 140 in the form of a bitstream, decodes the received audio signal into Pulse Code Modulation (PCM) format, and outputs the PCM signal to the noise suppressor (noise reduction unit) 173. In the present invention, the decoded audio signal may be a multimedia audio signal.

The noise suppressor 173 suppresses the noise component included in the received audio signal and outputs the noise-suppressed signal to the dynamic range controller 174. If Flag_ON is received from the hearing ability tester 171, the noise suppressor 173 performs noise gating and noise suppression. Herein, noise gating is a function that removes the noise component added to the received audio signal (i.e., noise outside of the dynamic range). Flag_ON is a control signal requesting the optimization of the audio quality based on the hearing characteristics of the user.

More specifically, if Flag_ON is received from the hearing ability tester 171, the dynamic range controller 174 adjusts the preconfigured dynamic range to be suited for the hearing characteristic of the user. That is, the dynamic range controller 174 adjusts the dynamic range for each frequency using the auditory threshold. For example, when a user's auditory threshold is 20 dB at the frequency of 1 kHz, the dynamic range controller 174 analyzes the 1 kHz component among the frequency components of the received audio signal and, if the analysis result indicates that 1 kHz frequency component of the received signal has a size of 10 dB, the dynamic range controller 174 may adjust the size of the 1 kHz frequency component of the received signal from 10 dB to 20 dB or more, such as 25 dB. That is, because the dynamic range of the 1 kHz component is adjusted from 0-80 dB to 20-80 dB, and the analysis result indicates that the 1 kHz frequency component of the received signal has a size of 10 dB, which is outside the adjusted dynamic range of the 1 kHz component, the size of the 1 kHz frequency component of the received signal is adjusted from 10 dB to 20 dB or more, which is within the adjusted dynamic range of the 1 kHz component. For example, before adjusting the dynamic range, there are 80 levels between 0 and 80 dB. After adjusting the dynamic range, there are 60 levels between 20 and 80 dB. However, since the input audio signal can be one of 0-80 dB, 80 levels between 20 and 80 dB are needed. For example, the width of each level is therefore 0.75 dB. Then 10 dB are needed to convert to 20+(0.75*10 dB)=27.5 dB.

Similarly, when the user's auditory threshold is 10 dB at the frequency of 2 kHz, the dynamic range controller 174 analyzes the 2 kHz component among the frequency components of the received audio signal and, if the analysis result indicates that the 2 kHz frequency component of the received signal has a size of 5 dB, the dynamic range controller 174 may adjust the size of the 2 kHz frequency component from 5 dB to 10 dB or more such as 13 dB. That is, because the dynamic range of the 2 kHz component is adjusted from 0-80 dB to 10-80 dB, and the size of the of the 2 kHz frequency component is 5 dB, which is outside the adjusted dynamic range, the dynamic range controller 174 adjusts the size of the of the 2 kHz frequency component from 5 dB to 10 dB or more, which is within the adjusted dynamic range.

The procedure is performed for all frequency components so that the received audio signal is automatically adjusted in adaptation to a user's auditory thresholds for each frequency.

If Flag_ON is not received from the hearing ability tester 171, the dynamic range controller 174 delivers the received audio signal to the sound pressure adjuster 175 without adjustment.

The sound pressure adjuster 175 automatically adjusts the sound pressure of the received audio signal from the dynamic range controller 174, with or without adjustment in dynamic range, according to the preconfigured sound pressure output characteristic and outputs the sound pressure-adjusted audio signal to the tone color adjuster 176. For example, an audio signal may be preconfigured to output within a sound pressure range from 7 dB to 80 dB. When the received audio signal has a sound pressure of 40 dB, the sound pressure adjuster 175 may output the received audio signal without sound pressure adjustment. When the received audio signal has a sound pressure of 90 dB, the sound pressure adjuster 175 may lower the sound pressure of 90 dB to 80 dB and output the received audio signal with the lowered sound pressure of 80 dB. When the received audio signal has a sound pressure of 5 dB, the sound pressure adjuster 175 may increase the sound pressure of 5 dB to 7 dB and output the received audio signal with the increased sound pressure of 7 dB. That is, the sound pressure adjuster 175 automatically matches the size of the signal to the preconfigured sound pressure output characteristic in the time domain.

The tone color adjuster 176 adjusts the tone color of the received audio signal by applying a filter coefficient satisfying a predefined frequency response and outputs the tone color-adjusted audio signal to the audio processing unit 150.

Alternatively, the sound pressure adjuster 175 and the tone color adjuster 176 may be omitted. That is, the received audio signal output by the dynamic range controller 174 can be input directly to the audio processing unit 150, without adjustment in sound pressure and tone color.

Figure 4:
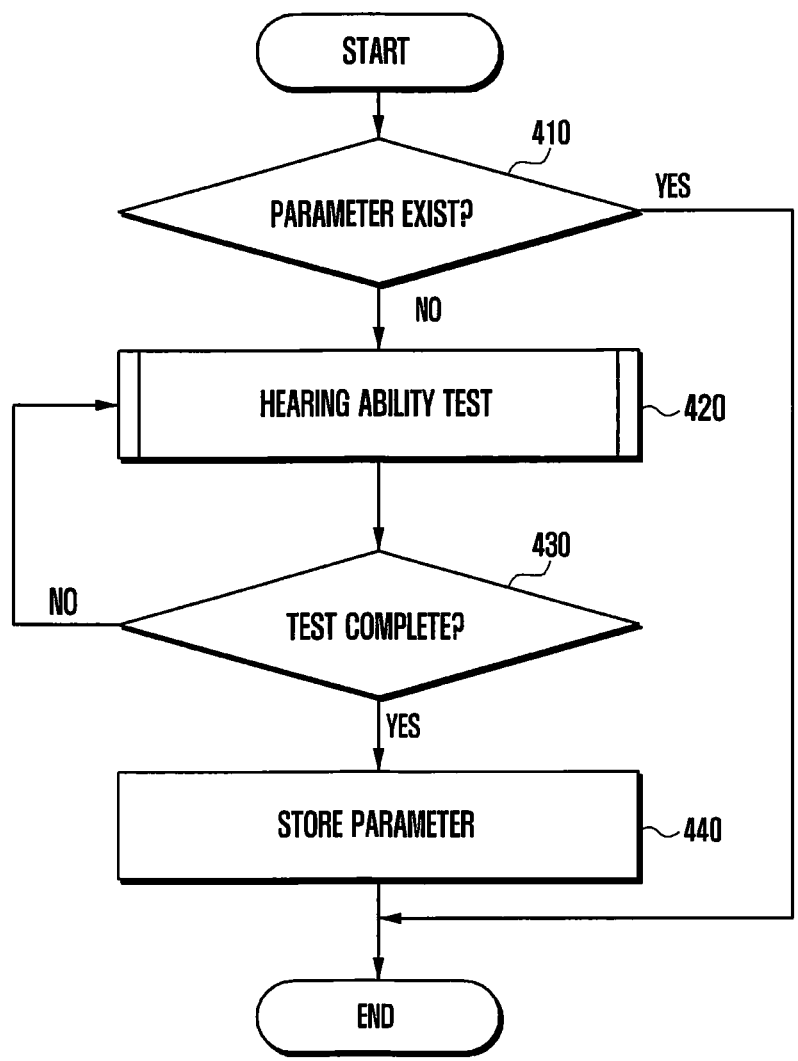
FIG. 4 is a flow chart illustrating a hearing ability test method according to an embodiment of the present invention.

FIG. 4 is a flow chart illustrating a hearing ability test method according to an embodiment of the present invention.

Referring to FIG. 4, the control unit 170 determines whether there is a parameter for changing the dynamic range in step 410. If the parameter is not included in the storage unit 130, the control unit 170 may perform hearing ability test in step 420. If the parameter is included in the storage unit 130, the control unit 170 may not perform the hearing ability test. The hearing ability test may be performed in response to a user request.

In step 430, the control unit 170 determines whether the hearing ability test is completed. For example, the control unit 170 controls the touchscreen 110 to display a "restart" button and a "done" button. If the "done" button is selected by the user, the control unit 170 determines that the hearing ability test is completed in step 430 and stores the parameter generated from the hearing ability test in the storage unit 130 in step 440.

Figure 5:
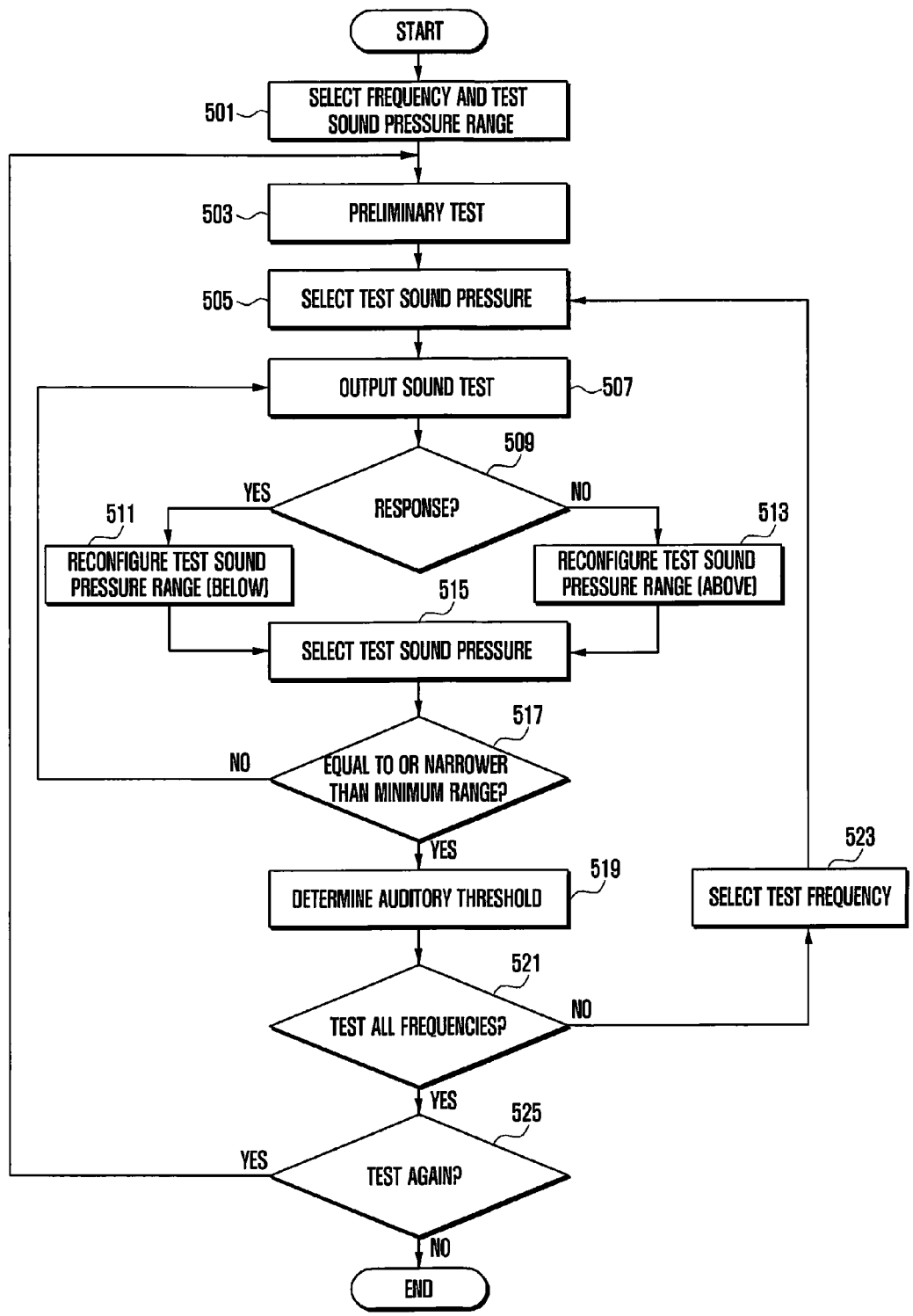
FIG. 5 is a flow chart illustrating a hearing ability test method according to an embodiment of the present invention.

FIG. 5 is a flow chart illustrating a hearing ability test method according to an embodiment of the present invention. Specifically, FIG. 5 illustrates the hearing ability test step 420 of FIG. 4 in more detail.

Referring to FIG. 5, the control unit 170 detects the user's hearing ability test request. For example, the control unit 170 detects the tap on a settings icon on the touchscreen 110. The touchscreen 110 displays the settings menu screen having the icons of the functions related to the hearing test under the control of the control unit 170. The control unit 170 selects a hearing test target frequencies and a test sound pressure range according to the hearing ability test request of the user (e.g. tap on the icon) at step 501. For example, the hearing test target frequencies may be 250 Hz, 500 Hz, 1 kHz, 2 kHz, 4 kHz, and 8 kHz, and the test sound pressure range may be 0 dB to 80 dB.

If the user's test start request (e.g. tap on the 'start' button) is detected, a preliminary test is performed in step 503. In the preliminary test, the control unit 170 first sets the test sound pressure to (0+80)/2=40 dB, outputs the test sound of 40 dB per test frequency to the audio processing unit 150 at an interval (e.g., 1 second), and stores the user response result in the storage unit 130. For example, the user may respond to the respective test sounds, i.e., indicate whether or not the test sound can be heard, as (250 Hz, 40 dB)=NO, (500 Hz, 40 dB)=YES, (1 kHz, 40 dB)=YES, (2 kHz, 40 dB)=YES, (4 kHz, 40 dB)=NO, and (8 kHz, 40 dB)=NO. These response results are then stored in the storage unit 130. The control unit 170 reconfigures the test sound range and stores the reconfiguration result in the storage unit 130. Thereafter, the control unit 170 selects the test frequency for use in the hearing ability test.

In step 505, the control unit 170 selects the test sound pressure. More specifically, the control unit 170 reads the test sound pressure range of the selected test frequency from the storage unit 130. Next, the control unit selects the test sound pressure at the center of the test sound pressure range. For example, if the test frequency is 250 Hz and the test sound pressure range for 250 Hz is 40 dB to 80 dB, from the preliminary test result, the center of the test sound pressure range, i.e., 60 dB, is selected as the test sound pressure.

In step 507, the control unit 170 outputs the test sound corresponding to the selected test frequency and the selected test sound pressure to the audio processing unit 150.

In step 509, the control unit 170 determines whether the user responds to the test sound. For example, the user can input a user input of "yes" when the sound is heard, or "no" when the sound is not heard. Alternatively, if a key input is entered within 1 second of the output of the test sound, the control unit 170 determines that the user has heard the test sound and, otherwise, after the 1 second, the control unit 170 determines that the user has not heard the test sound.

FIG. 6 illustrates examples of screens displayed to a user during a hearing ability test according to an embodiment of the present invention.

Referring to FIG. 6, the control unit 170 displays a message "Can you hear the beep?", as illustrated in screen (a) of FIG. 6. If the YES button is selected in response to the message, the control unit 170 determines that the user has heard the test sound. If the NO button is selected, the control unit 170 determines that the user has not heard the test sound.

Referring again to FIG. 5, if the user hears the test sound in step 509, the control unit 170 stores the response result in the storage unit 130 and reconfigures the range below the test sound pressure, as a new test sound pressure range, in step 511. For example, if the user hears the test sound of [250 Hz, 60 dB], the control unit 170 resets the test sound pressure range at 250 Hz to 40 dB to 60 dB.

If the user does not hear the test sound in step 509, the control unit 170 stores the response result in the storage unit 130 and reconfigures the range above the test sound pressure, i.e. from 60 dB to 80 dB, as a new test sound pressure range, in step 513.

In step 515, the control unit 170 selects the test sound pressure of the test sound to be output next. For example, the test sound pressure of 50 dB is selected for the reconfigured test sound pressure range of 40 dB to 60 dB, and the test sound pressure of 70 dB is selected for the reconfigured test sound pressure range of 60 dB to 80 dB.

In step 517, the control unit 170 determines whether the reconfigured test sound pressure range, i.e., the range having the auditory threshold, is narrower than a predetermined minimum range, e.g., 5 dB. If the reconfigured test sound pressure range is greater than or equal to 5 dB, the procedure returns to step 507.

If the reconfigured test sound pressure range is less than 5 dB, the control unit 170 determines the reconfigured test sound pressure range as the auditory threshold at the corresponding frequency and stores the auditory threshold in the storage unit 130 in step 519.

In step 521, the control unit 170 determines whether the auditory threshold is determined at all of test frequencies.

If the auditory threshold is not determined at each test frequency, the control unit 170 selects a next test frequency in step 523, and steps 505 to 521 are repeated for the next test frequency.

For example, the control unit 170 may randomly select one of the non-tested frequencies in step 523. That is, the control unit 170 can shuffle the order of the non-tested frequencies and randomly select a frequency to be tested next. If the frequencies are shuffled to the order of 250 Hz, 1 kHz, 8 kHz, 500 Hz, 4 kHz, and 2 kHz, and if the 250 Hz is determined as the auditory threshold, 1 kHz is selected as the next frequency to be tested.

If the auditory threshold is determined at each test frequency in step 521, the control unit 170 determines whether to perform a retest in step 525. For example, if the auditory thresholds of all of the test frequencies are determined, the control unit 170 controls the touchscreen 110 to display a test result screen, as illustrated in screen (b) of FIG. 6.

Referring again to FIG. 6, upon detecting the selection of the "done" button 610, the control unit 170 ends the test and stores the auditory threshold in the storage unit 130. However, upon detecting the selection of the "restart" button 620, the control unit 170 performs the test again.

Additionally, the control unit 170 may ask the user whether or not to apply the test result, as illustrated in screen (b) of FIG. 6. For example, if the "no" button 630 and the "done" button are selected, the control unit 170 stores the auditory threshold, but does not perform telephony audio quality optimization. If the "optimized for left ear" item 640 or "optimized for right ear" item 650, and the "done" button 610 are selected, the control unit 170 stores the auditory thresholds and performs selected telephony audio quality optimization using the stored auditory thresholds.

Although FIG. 5 illustrates the preliminary test in step 503 being performed at individual test frequencies in series, the test procedure may be performed without the preliminary test.

Figure 7:
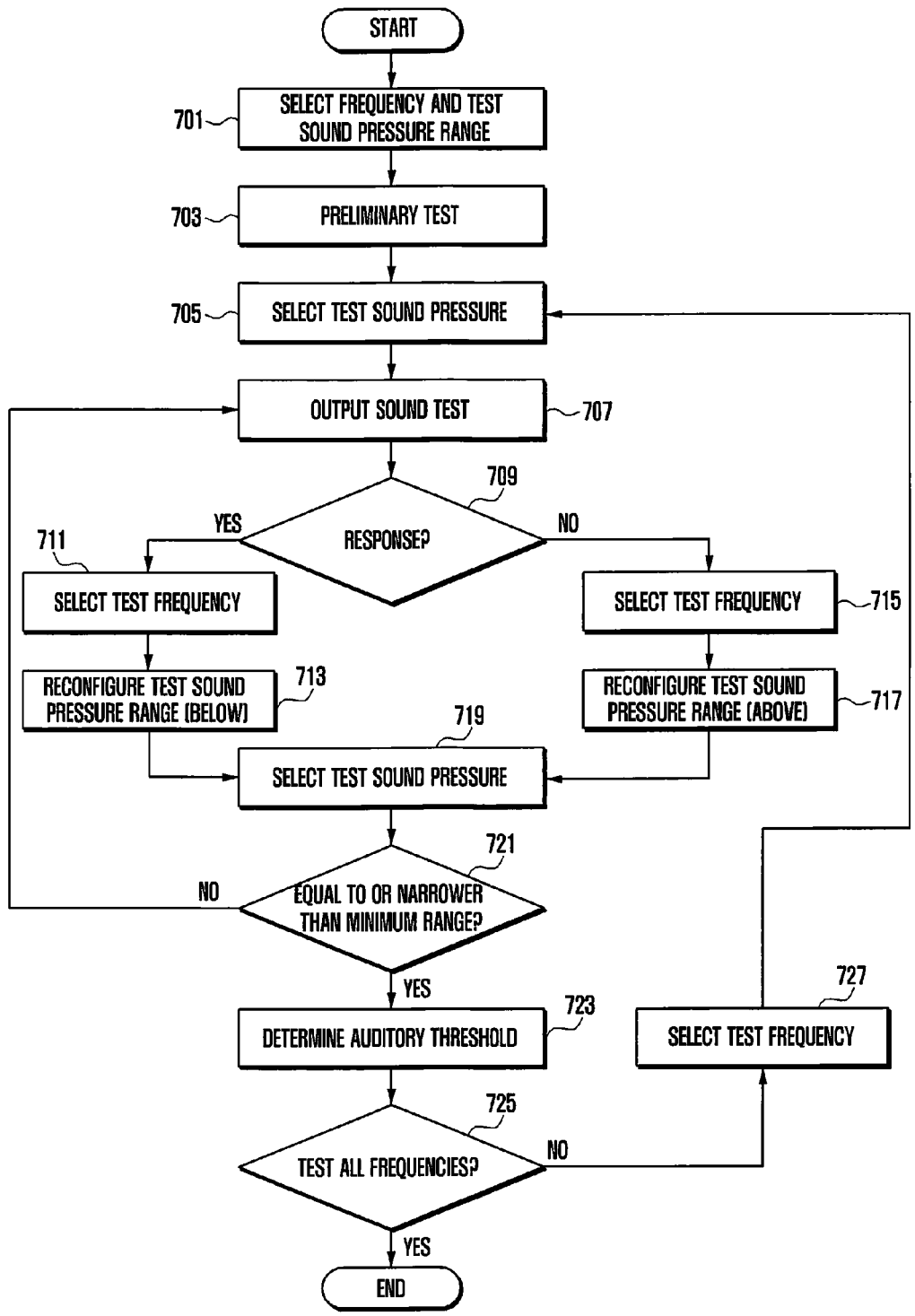
FIG. 7 is a flowchart illustrating a hearing ability test method according to an embodiment of the present invention.

FIG. 7 is a flowchart illustrating a hearing ability test method according to an embodiment of the present invention. In FIG. 7, steps 701 to 709 are the same as steps 501 to 509 in FIG. 5. Accordingly, a repetitive description of these steps will be avoided in the description of FIG. 7.

Referring to FIG. 7, if the user hears the test sound in step 709, the control unit 170 randomly selects a test frequency of the test sound to be output in step 711. More specifically, the control unit 170 rules out test frequencies at which the auditory threshold has been determined, and randomly selects a frequency among the remaining frequencies. The control unit 170 stores the user response to the test sound output in step 707 and reconfigures the region below the test sound pressure as the test sound pressure range of the corresponding test frequency in step 713.

If the user does not hear the test sound in step 709, the control unit 170 randomly selects the test frequency of the test sound to be output next in step 715. As described above, the control unit 170 rules out test frequencies at which the auditory threshold has been determined, and randomly selects a frequency among the remaining frequencies. The control unit 170 stores the user response to the test sound output in step 707 and reconfigures the region above the test sound pressure as the test sound pressure range of the corresponding test frequency in step 717.

In step 719, the control unit 170 selects the center sound pressure of the current test sound pressure range of the test frequency (selected in step 711 or 715) as the test sound pressure.

In step 721, the control unit 170 determines whether the test sound pressure range, i.e., the region having the auditory threshold less than or equal to a predetermined minimum range (e.g., 5 dB).

If the test sound pressure range is greater than 5 dB, the procedure returns to step 707, and the control unit 170 performs the binary search process on the test frequency selected in step 711 or 715.

If the test sound pressure range is less than or equal to 5 dB, the control unit 170 determines the test sound pressure range configured for the test frequency selected in step 711 or 715 as the auditory threshold of the corresponding frequency, and then stores the auditory threshold in the storage unit 130 in step 723. For example, if the current test sound pressure range configured at 1 kHz is from 55 dB to 60 dB, i.e., 5 dB, the auditory threshold at 1 kHz becomes 57.5 dB. Accordingly, the test sound pressure selected in step 719 is determined as the auditory threshold.

The control unit 170 determines whether or not the auditory thresholds of all of the test frequencies are determined in step 725. If the auditory thresholds of all of the test frequencies are determined, the control unit 170 ends the test.

If the auditory thresholds of all of the test frequencies are not determined, the control unit 170 randomly selects the next test frequency in step 727, and the procedure returns to step 705 to test the next frequency. As described above, the control unit 170 rules out test frequencies at which the auditory threshold has been determined, and randomly selects a frequency among the remaining frequencies.

Although FIG. 7 illustrates a preliminary test being performed at individual test frequencies in series, the test procedure may be performed without the preliminary test.

Unlike FIG. 5, in which the test frequency is changed after the determination of the auditory threshold, in FIG. 7, the test frequency is changed randomly, regardless of the determination of the auditory threshold.

In FIG. 5, because a next sound is produced at an expected interval, a user may incorrectly perceive that the next test sound is heard. Because the test frequency and the test sound pressure change at every test, the hearing ability test method in FIG. 7 is more effective than the descending method, ascending method, the hybrid method, and the method illustrated FIG. 5 in preventing the user from predicting the next test sound.

Figure 8:
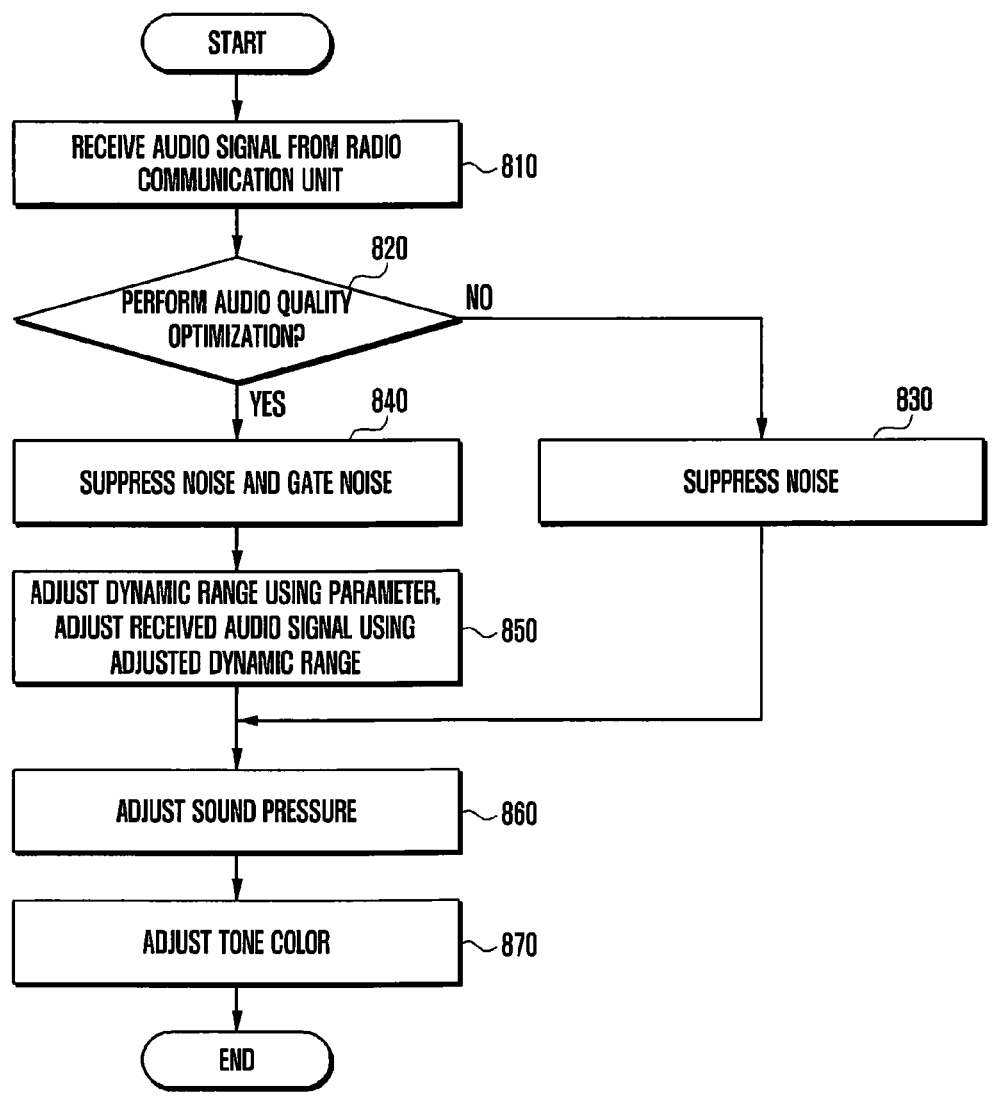
FIG. 8 is a flowchart illustrating a method for optimizing telephony audio quality to a user according to an embodiment of the present invention.

FIG. 8 is a flowchart illustrating a method for optimizing telephony audio quality to a user according to an embodiment of the present invention.

Referring to FIG. 8, in step 810, the control unit 170 receives the audio signal in the form of a bitstream from the radio communication unit 140 and decodes the received audio signal into Pulse Code Modulation (PCM) format. In step 820, the control unit 170 determines whether to perform the telephony audio quality optimization. For example, if a parameter (e.g., an auditory threshold) is stored in the storage unit 130, the control unit 170 determines to perform the telephony audio quality optimization. If there is no auditory threshold stored in the storage unit 130, the control unit 170 determines not to perform the telephony audio quality optimization.

Alternatively, whether or not to perform the telephony audio quality optimization may be determined by the user.

Figure 9:
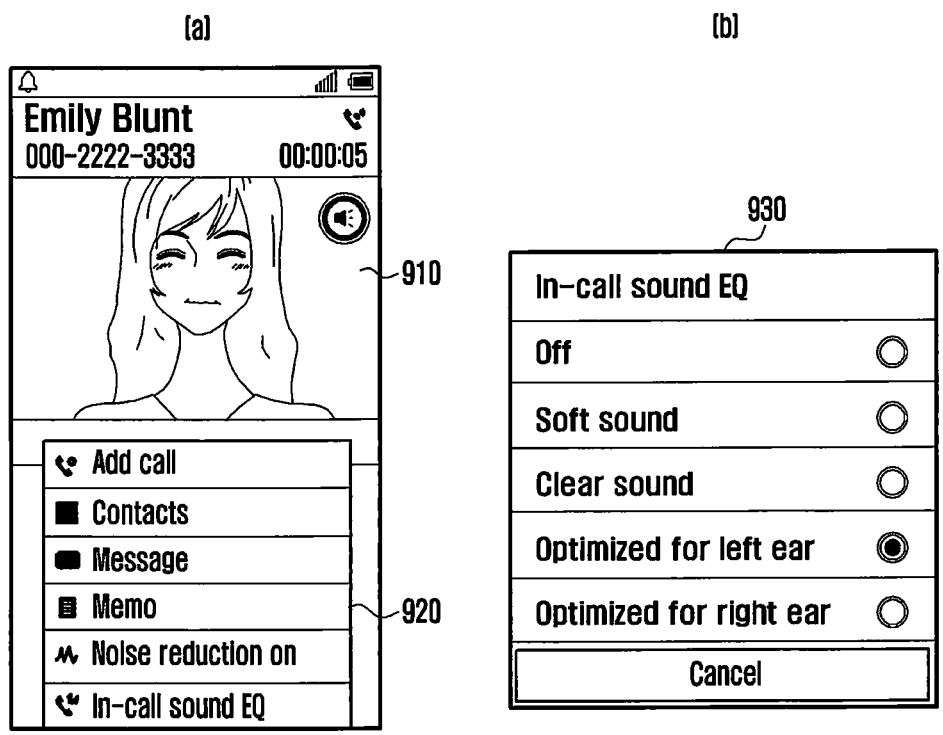
FIG. 9 illustrates examples of screens displayed to a user for optimizing an in-call sound setting according to an embodiment of the present invention.

FIG. 9 illustrates examples of screens displayed to a user for optimizing an in-call sound setting according to an embodiment of the present invention.

Referring to FIG. 9, the telephony audio quality optimization may be determined during telephony communication.

More specifically, referring to screen (a) in FIG. 9, the control unit 170 controls the touchscreen 110 to display the telephony screen 910. The telephony screen 910 includes profile photo of the counterparty. Upon detection of a menu call key selection, the control unit 170 controls the touchscreen 110 to display a first menu 920 on the telephony screen 910. The control unit 170 detects the selection of "In-call sound EQ" item of the first menu 920 and controls the touchscreen 110 to display the second menu 930, as illustrated in screen (b) of FIG. 9, which is related to the equalizer on the telephony screen 910.

The second menu 930 includes an EQ off item, a soft sound item, a clear sound item, an "optimized for left ear" item, and an "optimized for right ear" item. If one of the "optimized for left ear" and "optimized for right ear" items is selected, the control unit 170 determines to perform the telephony audio quality optimization for the selected ear.

Figure 10:
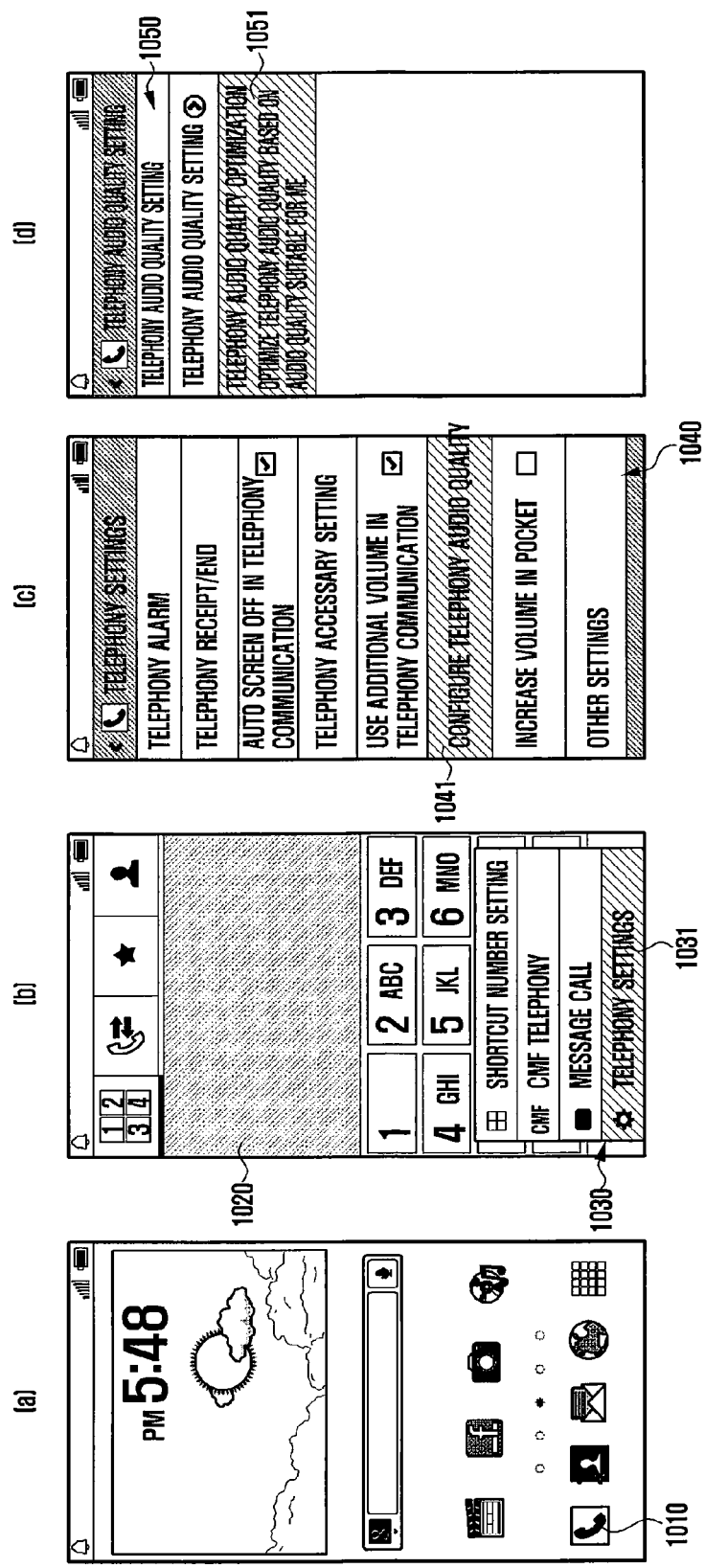
FIG. 10 illustrates examples of screens displayed to a user for setting telephony audio quality according to an embodiment of the present invention.

FIG. 10 illustrates examples of screens displayed to a user for setting telephony audio quality according to an embodiment of the present invention.

Referring to FIG. 10, the telephony audio optimization may be determined before the start of telephony communication. In screen (a) of FIG. 10, the touchscreen 110 displays a telephony button 1010 under the control of the control unit 170. When the telephony button 1010 is selected, the control unit 170 controls the touchscreen 110 to display the telephony screen 1020, as illustrated in screen (b) of FIG. 10. When a menu call key is selected, the control unit 170 controls the touchscreen 110 to display the telephony setting menu 1030 on the telephony screen 1020. When a telephony setting button 1031 is selected from the telephony menu 1020, the control unit 170 controls the touchscreen 110 to display the telephony setting screen 1040, as illustrated in screen (c) of FIG. 10.

When a telephony audio quality setting button 1041 is selected on the telephony setting screen 1040, the control unit 170 controls the touchscreen 110 to display a telephony audio quality setting screen 1050, as illustrated in screen (d) of FIG. 10. When a telephony audio quality optimization button 1051 is selected on the telephony audio quality setting screen 1050, the control unit 170 determines to perform the telephony audio quality optimization.

Referring again to FIG. 8, if telephony audio quality optimization is not to be performed in step 820, the control unit 170 suppresses the noise component included in the received audio signal in step 830. However, if telephony audio quality optimization is to be performed in step 820, the control unit 170 performs noise gating along with noise suppression in step 840. In step 850, the control unit 170 adjusts the dynamic range for each test frequency using a parameter (e.g., an auditory threshold) read from the storage unit 130 and adjusts the noise-suppressed and noise-gated audio signal using the adjusted per-frequency dynamic ranges.

In step 860, the control unit 170 adjusts the sound pressure of the audio signal, which has been noise-suppressed in step 830 or adjusted in step 850, to be suited for a predetermined sound pressure output characteristic. In step 870, the control unit applies a filter coefficient satisfying a predetermined frequency response to the received audio signal to adjust the tone color of the received audio signal and then outputs the tone color-adjusted audio signal to the audio processing unit 150. The audio processing unit 150 performs D/A conversion on the audio signal from the control unit 170, amplifies the analog audio signal, and outputs the amplified audio signal to the speaker (SPK).

Alternatively, the sound pressure adjustment in step 860 and the tone color adjustment in step 870 may be omitted. That is, the control unit 170 may output the received audio signal to the audio processing unit 150 without adjusting the sound pressure and the tone color.

A mobile device and method according to any of the above-described embodiments of the present invention are capable of processing a received audio signal in adaptation to hearing characteristics of a user, in order to output audio that is best-suited for the user.

The above-described audio signal processing methods according to embodiments of the present invention can be implemented in the form of computer-executable program commands and stored in a computer-readable storage medium. The computer readable storage medium may store the program commands, data files, and data structures in individual or combined forms. The program commands recorded in the storage medium may be designed and implemented for various embodiments of the present invention or used by those skilled in the computer software field. The computer-readable storage medium includes magnetic media such as a floppy disk and a magnetic tape, optical media including a Compact Disc (CD) ROM and a Digital Video Disc (DVD) ROM, a magneto-optical media such as a floptical disk, and the hardware device designed for storing and executing program commands such as ROM, RAM, and flash memory. The programs commands include the language code executable by computers using the interpreter as well as the machine language codes created by a compiler. The aforementioned hardware device can be implemented with one or more software modules for executing the operations of the various embodiments of the present invention.

While the present invention has been particularly shown and described with reference to certain embodiments thereof, it will be understood by those of ordinary skill in the art that various changes in form and details may be made therein without departing from the spirit and scope of the present invention as defined by the following claims and their equivalents.

What is claimed is:

1. A method for customizing audio data processing, the method comprising:
   receiving audio data through a wireless communication channel from an external device;
   decoding the received audio data;
   reducing noise of the decoded audio data;
   identifying hearing characteristics of a user by testing hearing abilities of the user at a plurality of frequency bands;
   adjusting a dynamic range of each of the plurality of frequency bands based on the hearing characteristics;
   processing the noise-reduced audio data based on the adjusted dynamic range of each of the plurality of frequency bands; and
   outputting the processed audio data.

2. The method of claim 1, wherein reducing the noise of the decoded audio data comprises:
   determining whether or not audio quality optimization is to be performed;
   if the audio quality optimization is not to be performed, suppressing the noise included in the decoded audio data; and if the audio quality optimization is to be performed, suppressing the noise included in the decoded audio data and removing noise outside of the dynamic range from the decoded audio data.

3. The method of claim 1, wherein testing the hearing abilities comprises identifying an auditory threshold for each of the plurality of frequency bands.

4. The method of claim 3, wherein identifying the auditory threshold for each of the plurality of frequency bands comprises:
selecting one of the plurality of frequency bands as a test frequency;
selecting a test sound pressure from a test sound pressure region of the test frequency;
outputting a test sound corresponding to the selected test frequency and the selected test sound pressure;
receiving a user response to the test sound;
dividing the test sound pressure region of the test frequency into an auditory threshold absence region and an auditory threshold presence region, based on the received user response and the selected test sound pressure;
determining if the auditory threshold presence region is within a predetermined minimum range; and
determining the auditory threshold based on the auditory threshold presence region, when the auditory threshold presence region is within the predetermined minimum range.

5. The method of claim 4, wherein when the auditory threshold presence region is not within the predetermined minimum range, testing the hearing abilities of the user further comprises:
repeatedly reconfiguring the auditory threshold presence region as a reconfigured test sound pressure region of the test frequency, selecting a second test sound pressure from the reconfigured test sound pressure region of the test frequency, outputting a second test sound corresponding to the selected test frequency and the selected second test sound pressure, receiving a second user response to the second test sound, and dividing the reconfigured test sound pressure region of the test frequency into the auditory threshold absence region and the auditory threshold presence region, based on the received second user response and the selected second test sound pressure, until the auditory threshold presence region is within the predetermined minimum range; and
determining the auditory threshold based on the auditory threshold presence region, when the auditory threshold presence region is within the predetermined minimum range.

6. The method of claim 4, wherein determining the auditory threshold based on the auditory threshold presence region comprises setting the auditory threshold as one of a lower limit of the auditory threshold presence region, an upper limit of the auditory threshold presence region, and an average of the lower limit of the auditory threshold presence region and the upper limit of the auditory threshold presence region.

7. The method of claim 4, wherein determining the auditory threshold based on the auditory threshold presence region comprises setting the auditory threshold as one of a lower limit of the auditory threshold presence region, an upper limit of the auditory threshold presence region, and an average of the lower limit of the auditory threshold presence region and the upper limit of the auditory threshold presence region.

8. The method of claim 1, wherein adjusting the dynamic range of each of the plurality of frequency bands comprises adjusting one of an upper limit and a lower limit of the dynamic range of each of the plurality of frequency bands, based on the auditory threshold for each of the plurality of frequency bands, respectively.

9. The method of claim 8, further comprising receiving a user input to adjust the decoded audio data based on the adjusted dynamic range of each of the plurality of frequency bands.

10. An apparatus for customizing audio data processing, the apparatus comprising:
a radio communication unit which receives audio data through a wireless communication channel from an external device;
a speaker; and
a controller configured to decode the audio data received by the radio communication unit, reduce noise of the decoded audio data, test hearing characteristics of a user at a plurality of frequency bands, adjust a dynamic range of each of the plurality of frequency bands based on results of the testing, adjust the noise-reduced audio data based on the adjusted dynamic range of each of the plurality of frequency bands, and output the adjusted audio data to the user via the speaker.

11. The apparatus of claim 10, wherein the controller is further configured to reduce the noise of the decoded audio data by:
determining whether or not audio quality optimization is to be performed;
if the audio quality optimization is not to be performed, suppressing the noise included in the decoded audio data; and
if the audio quality optimization is to be performed, suppressing the noise included in the decoded audio data and removing noise outside of the dynamic range from the decoded audio data.

12. The apparatus of claim 10, wherein the results of the testing comprise an auditory threshold for each of the plurality of frequency bands.

13. The apparatus of claim 12, wherein the controller is configured to test the hearing characteristics of the user by:
selecting one of the plurality of frequency bands as a test frequency;
selecting a test sound pressure from a test sound pressure region of the test frequency;
outputting a test sound corresponding to the selected test frequency and the selected test sound pressure;
receiving a user response to the test sound;
dividing the test sound pressure region of the test frequency into an auditory threshold absence region and an auditory threshold presence region, based on the received user response and the selected test sound pressure;
determining if the auditory threshold presence region is within a predetermined minimum range; and
determining the auditory threshold based on the auditory threshold presence region, when the auditory threshold presence region is within the predetermined minimum range.

14. The apparatus of claim 13, wherein when the auditory threshold presence region is not within the predetermined minimum range, the controller is configured to test the hearing characteristics of the user by:
repeatedly reconfiguring the auditory threshold presence region as a reconfigured test sound pressure region of the test frequency, selecting a second test sound pressure from the reconfigured test sound pressure region of the test frequency, outputting a second test sound corresponding to the selected test frequency and the selected second test sound pressure, receiving a second user response to the second test sound, and dividing the reconfigured test sound pressure region of the test frequency into the auditory threshold absence region and the auditory threshold presence region, based on the received second user response and the selected second test sound pressure, until the auditory threshold presence region is within the predetermined minimum range; and determining the auditory threshold based on the auditory threshold presence region, when the auditory threshold presence region is within the predetermined minimum range.

15. The apparatus of claim 13, wherein the controller is configured to determine the auditory threshold based on the auditory threshold presence region by setting the auditory threshold as one of a lower limit of the auditory threshold presence region, an upper limit of the auditory threshold presence region, and an average of the lower limit of the auditory threshold presence region and the upper limit of the auditory threshold presence region.

16. The apparatus of claim 13, wherein the controller is configured to determine the auditory threshold based on the auditory threshold presence region by setting the auditory threshold as one of a lower limit of the auditory threshold presence region, an upper limit of the auditory threshold presence region, and an average of the lower limit of the auditory threshold presence region and the upper limit of the auditory threshold presence region.

17. The apparatus of claim 10, wherein controller is configured to adjust the dynamic range of each of the plurality of frequency bands by adjusting one of an upper limit and a lower limit of the dynamic range of each of the plurality of frequency bands, based on the auditory threshold for each of the plurality of frequency bands, respectively.

18. The apparatus of claim 10, further comprising an input device configured to receive a user input commanding the controller to adjust the decoded audio data based on the adjusted dynamic range of each of the plurality of frequency bands.

* * * * *